US012649034B2

(12) United States Patent
Reinhart et al.

(10) Patent No.: US 12,649,034 B2
(45) Date of Patent: Jun. 9, 2026

(54) AEROSOL DELIVERY DEVICE AND METHOD OF OPERATING THE AEROSOL DELIVERY DEVICE

(71) Applicant: PARI Pharma GmbH, Starnberg (DE)

(72) Inventors: Markus Reinhart, Utting (DE);
Matthias Finke, Planegg (DE);
Wolfgang Achtzehner, Alling (DE)

(73) Assignee: PARI Pharma GmbH, Starnberg (DE)

( * ) Notice: Subject to any disclaimer, the term of this patent is extended or adjusted under 35 U.S.C. 154(b) by 1119 days.

(21) Appl. No.: 17/413,119

(22) PCT Filed: Dec. 13, 2019

(86) PCT No.: PCT/EP2019/085092
§ 371 (c)(1),
(2) Date: Jun. 11, 2021

(87) PCT Pub. No.: WO2020/120744
PCT Pub. Date: Jun. 18, 2020

(65) Prior Publication Data
US 2022/0047818 A1      Feb. 17, 2022

(30) Foreign Application Priority Data
Dec. 14, 2018    (EP) .................................... 18212621

(51) Int. Cl.
*A61M 11/00*          (2006.01)
(52) U.S. Cl.
CPC ... *A61M 11/005* (2013.01); *A61M 2205/0294* (2013.01); *A61M 2205/3368* (2013.01)
(58) Field of Classification Search
CPC .. A61M 11/005; B05B 17/06; B05B 17/0607; B05B 17/0646
See application file for complete search history.

(56) References Cited

U.S. PATENT DOCUMENTS 3,391,547 A     7/1968  Kingston
5,803,362 A  *  9/1998  Fraccaroli ......... A61M 15/0085
                                                    239/338

(Continued)

FOREIGN PATENT DOCUMENTS

DE        29501569 U1  *  2/1995  ............. B05B 17/06
DE        199 53 317 C1     2/2001
(Continued)

OTHER PUBLICATIONS

Machine language translation of German patent DE29501569U1, filed Feb. 2, 1995; retrieved from worldwide.espacenet.com/patent/search/family/008003248/publication/DE29501569U1?q=pn%3DDE29501569U1 (Year: 1995).*

(Continued)

*Primary Examiner* — Victoria Murphy
(74) *Attorney, Agent, or Firm* — Wolf, Greenfield & Sacks, P.C.

(57)          ABSTRACT
The invention relates to an aerosol delivery device (A) comprising an aerosol generator for generating an aerosol in the aerosol delivery device (A). The aerosol generator comprises a membrane (1) and a vibrator (7) which is configured to vibrate a fluid (3) and to aerosolise the fluid (3) by the membrane (1). The aerosol delivery device (A) further comprises a fluid reservoir (2) for receiving the fluid (3) to be aerosolised, wherein the fluid reservoir (2) is arranged in fluid communication with the membrane (1). Moreover, the aerosol delivery device (A) comprises a controller (10) which is configured to operate the vibrator (7) so as to vibrate the fluid (3), a temperature sensor (13) which is configured to detect a temperature of the vibrator (7) and/or the membrane (1), and a detector (13a) which is configured to detect the presence of fluid (3) in contact with the membrane (1) and/or in the fluid reservoir (2) on the basis of the temperature of the vibrator (7) and/or the
(Continued)

membrane (1) detected by the temperature sensor (13). Further, the invention relates to a method of operating such an aerosol delivery device (A).

18 Claims, 4 Drawing Sheets

(56)                    References Cited

U.S. PATENT DOCUMENTS

| | | | |
|---|---|---|---|
| 6,546,927 | B2 | 4/2003 | Litherland et al. |
| 6,901,926 | B2 | 6/2005 | Yamamoto et al. |
| 8,779,402 | B2 * | 7/2014 | Yabu ................... B05B 17/0607 |
| | | | 250/493.1 |
| 10,244,791 | B2 * | 4/2019 | Cameron ................. B05B 12/12 |
| 10,744,277 | B2 | 8/2020 | Finke et al. |
| 11,278,683 | B2 * | 3/2022 | Hetzer .............. A61M 15/0085 |
| 11,547,822 | B2 * | 1/2023 | Knoch .............. A61M 16/0003 |
| 11,610,473 | B2 * | 3/2023 | Finke ..................... G16H 40/67 |
| 11,707,758 | B2 * | 7/2023 | Schulz .............. A61M 15/0085 |
| | | | 239/102.1 |
| 11,839,891 | B2 * | 12/2023 | Grehan .............. A61M 15/0085 |
| 11,918,731 | B2 * | 3/2024 | Porter .............. A61M 16/0672 |
| 2004/0045547 | A1 | 3/2004 | Yamamoto et al. |
| 2004/0231665 | A1 * | 11/2004 | Lieberman ........ A61M 15/0086 |
| | | | 128/200.14 |
| 2006/0102172 | A1 * | 5/2006 | Feiner ............... A61M 15/0085 |
| | | | 128/200.14 |
| 2007/0202051 | A1 | 8/2007 | Schuschnig |
| 2007/0277816 | A1 * | 12/2007 | Morrison ............ B05B 17/0615 |
| | | | 128/200.16 |
| 2009/0056708 | A1 | 3/2009 | Stenzler et al. |
| 2012/0285236 | A1 * | 11/2012 | Haartsen ........... A61M 15/0065 |
| | | | 73/204.11 |
| 2014/0145000 | A1 | 5/2014 | Verschueren |
| 2014/0263721 | A1 * | 9/2014 | Schulz .............. A61M 15/0018 |
| | | | 239/102.1 |
| 2015/0174348 | A1 * | 6/2015 | Tunnell ............... A61M 16/021 |
| | | | 128/200.14 |
| 2015/0231340 | A1 | 8/2015 | Pumphrey et al. |
| 2015/0320944 | A1 | 11/2015 | Grehan et al. |
| 2016/0310681 | A1 * | 10/2016 | Finke ........................ A61P 1/08 |
| 2018/0161525 | A1 * | 6/2018 | Liu ..................... B05B 17/0661 |
| 2018/0236478 | A1 * | 8/2018 | Schulz .............. A61M 15/0085 |
| 2019/0054257 | A1 * | 2/2019 | Cameron ............. A61M 11/042 |
| 2019/0160234 | A1 * | 5/2019 | Lefkowitz ........... A61M 11/041 |
| 2020/0129813 | A1 | 4/2020 | Shindo et al. |
| 2022/0118198 | A1 * | 4/2022 | Knoch .............. A61M 16/1065 |
| 2023/0119086 | A1 * | 4/2023 | Knoch .............. A61M 15/0085 |
| | | | 128/200.16 |
| 2024/0066542 | A1 * | 2/2024 | Grehan .............. B05B 17/0669 |

FOREIGN PATENT DOCUMENTS

| | | | |
|---|---|---|---|
| DE | 10 2008 054 431 | B3 | 6/2010 |
| EP | 0 432 992 | A1 | 6/1991 |
| WO | WO 89/06657 | A1 | 7/1989 |
| WO | WO 92/22315 | A1 | 12/1992 |
| WO | WO 95/32992 | A1 | 12/1995 |
| WO | WO 00/47623 | A1 | 8/2000 |
| WO | WO 2004/039442 | A1 | 5/2004 |
| WO | WO 2005/029216 | A2 | 3/2005 |
| WO | WO 2006/094796 | A1 | 9/2006 |
| WO | WO 2008/029216 | A1 | 3/2008 |
| WO | WO 2010/139442 | A1 | 12/2010 |
| WO | WO 2015/091356 | A1 | 6/2015 |

OTHER PUBLICATIONS

International Search Report and Written Opinion mailed Feb. 10, 2020 in connection with International Application No. PCT/EP2019/085092.

International Preliminary Report on Patentability mailed Jun. 24, 2021 in connection with International Application No. PCT/EP2019/085092.

International Search Report and Written Opinion mailed Feb. 10, 2020 in connection with International Application No. PCT/EP2019/085173.

International Preliminary Report on Patentability mailed Jun. 24, 2021 in connection with International Application No. PCT/EP2019/085173.

* cited by examiner

AEROSOL DELIVERY DEVICE AND METHOD OF OPERATING THE AEROSOL DELIVERY DEVICE

RELATED APPLICATIONS

This Application is a national stage filing under 35 U.S.C. 371 of International Patent Application Serial No. PCT/EP2019/085092, filed Dec. 13, 2019, entitled "AEROSOL DELIVERY DEVICE AND METHOD OF OPERATING THE AEROSOL DELIVERY DEVICE". Foreign priority benefits are claimed under 35 U.S.C. § 119 (a)-(d) or 35 U.S.C. § 365(b) of European application number EP 18212621.9, filed Dec. 14, 2018. The entire contents of these applications are incorporated herein by reference in their entirety.

FIELD OF THE INVENTION

The invention relates to an aerosol delivery device comprising an aerosol generator with a membrane and a vibrator configured to vibrate a fluid and to aerosolise the fluid by the membrane and to a method of operating this aerosol delivery device.

BACKGROUND ART

Aerosols for therapeutic purposes are generated and delivered to a desired location within a user's or patient's body with aerosol delivery devices. A fluid or liquid (i.e., medicament) to be aerosolised or nebulised is supplied to an aerosol generator of the aerosol delivery device, the fluid or liquid is aerosolised or nebulised by the aerosol generator and the resultant aerosol is supplied to the user or patient.

The fluid or liquid may be aerosolised or nebulised in the aerosol generator by a membrane with through holes. The fluid or liquid may be in contact with the membrane via gravitational force or a supply system. The fluid or liquid may be supplied via a supply system, such as a vibratable slide, a vibratable plunger, a vibratable wall and/or a vibratable membrane.

The membrane may be a passive or an active membrane. In the case that the membrane is not vibrated by a vibrator, it is a passive membrane. The passive membrane may include a supply system and have, e.g., a vibrator in contact with a fluid reservoir, a wall, a channel plunger, and/or a supply system. In the case when the membrane is vibrated by a vibrator, it is an active membrane.

An inhalation nebuliser of the passive membrane type is disclosed in U.S. Pat. No. 6,901,926 B2 as well as in US 2004/0045547 A1, which describe, e.g., the nebulisers (inhalers) U1 and U22 from the company Omron. Further inhalation nebulisers of the passive membrane type are disclosed in US 121183747, WO 2006/094796 as well as in US 2009/0056708, which describe the Fox-POP, Medspray and Telemaq nebuliser technology. A further existing aerosol generator with a cantilever concept is disclosed in EP 0432992 A1 from the company Bespak.

An inhalation nebuliser of the active (vibrating) membrane type is disclosed in DE 199 53 317 C1, which describes, e.g., the eFlow inhalation device from the company PARI. The aerosol membrane generator described in this document comprises a cylindrical liquid storage container which is delimited at one end face by a membrane having the shape of a circular disc. A liquid disposed in the liquid storage container contacts the side of the membrane facing the container.

DE 199 53 317 C1 further discloses an oscillation generator, for example, a piezocrystal, which surrounds the membrane in a circular manner and is connected thereto such that the membrane can be caused to oscillate by means of the oscillation generator and an electric drive circuit. The liquid abutting the membrane on the one side is conveyed through holes in the oscillating membrane to the other side of the membrane and is emitted on this side into a mixing chamber as an aerosol.

Known from the utility model DE 295 01 569 is an ultrasonic liquid nebuliser having a piezocrystal which is caused to oscillate electrically by an oscillator circuit, the oscillator circuit being supplied by a power supply device.

DE 295 01 569 discloses an oscillator circuit which comprises a current limiting circuit and which is connected with an electronic temperature limiting circuit that compares a temperature-dependent electric signal occurring at the piezocrystal in a threshold circuit, the comparison signal of which activates a bi-stable circuit which blocks the oscillator when a limiting temperature in the piezocrystal is reached.

The disclosure of DE 295 01 569 is thereby directed at a protective mechanism for an ultrasonic liquid nebuliser in which the piezocrystal itself causes the liquid to oscillate and is in contact with a comparatively large amount of liquid. The liquid nebuliser described in DE 295 01 569 must furthermore accordingly use large currents in order to cause the large amount of liquid to oscillate.

Constant contact between the piezocrystal and the liquid is necessary owing to these large currents and the resulting large temperature differences in order to prevent destruction of the piezocrystal. If there is no longer any liquid present, the piezocrystal heats up very quickly and is destroyed if the oscillating circuit driving the nebuliser is not switched off immediately.

Only much smaller currents flow in inhalation nebulisers of the type described above, i.e., in inhalation nebulisers having membrane aerosol generators, and therefore only comparatively small temperature differences occur. In such inhalation nebulisers, the lack of liquid does not directly lead to heat-related damage to the piezoelectric elements.

Hence, the use of a protective mechanism such as described in DE 295 01 569 is not necessary in inhalation nebulisers of the type in question here and is not possible either owing to the much smaller currents.

However, it is also desirable in inhalation nebulisers having a membrane generator to reliably detect the presence of a liquid to be nebulised. This is because, on the one hand, the basis for a complete dosage delivery and high dosage accuracy could be thereby created and, on the other hand, it is possible to reliably indicate the end of a therapy session to the patient. Normally it is desired to generate aerosol from the whole liquid contained in a fluid reservoir to ensure appropriate and consistent dosing and ultimately inhalation therapy success. In particular, an early end of the therapy session, with remaining liquid in the reservoir, should be avoided. In addition, when adherence to therapy is monitored with a patient in telemedicine applications, the signal provides assurance that the entire liquid volume and dose has been nebulised and delivered. Furthermore, by immediately switching off the inhalation therapy device, it is possible, for example, to save power, e.g., increasing the lifetime of a battery.

EP 1 558 315 A1 discloses an inhalation therapy device including a membrane aerosol generator. A detection device is provided for determining whether a liquid to be nebulised is available. Determination of whether liquid is present or not occurs in the detection device by comparing the detected value of an electrical parameter of the membrane aerosol generator with a value for this parameter stored in the detection device. For this purpose, the detection device may use empirically determined values for the detected electrical parameter or a value of the electrical parameter which was detected in a previous cycle. This determination process may be independently and separately performed at different measurement frequencies.

However, this approach of determining the presence of liquid in the membrane aerosol generator is sensitive to the structural details of the membrane aerosol generator, such as the thickness and bonding of the piezo-element, and susceptible to external influences, such as the surface tension and the temperature of the liquid to be nebulised and the pressure in the liquid reservoir. These factors can affect the determination accuracy, so that the presence or absence of liquid in the membrane aerosol generator may not be reliably identified.

Also WO 2015/091356 A1 discloses an inhalation therapy device with a membrane aerosol generator, having a detection device for determining whether a liquid to be nebulised is available. A controller of the device is configured to sequentially operate a vibrator at a plurality of different vibration frequencies, while a sensor of the device is configured to detect an electrical parameter of the vibrator for each of the plurality of different vibration frequencies. Determination of whether or not liquid is present is performed by the detection device on the basis of the dependence of the detected values of the electrical parameter on the vibration frequency.

While this approach allows for the effect of structural details of the aerosol generator on the determination accuracy to be significantly reduced, this accuracy may still be affected by such influences to a certain degree.

Hence, there remains a need for an aerosol delivery device and an aerosol delivery method which allow for the presence of fluid or liquid to be aerosolised or nebulised to be reliably and efficiently detected.

SUMMARY OF THE INVENTION

An object of the invention is to provide an aerosol delivery device which enables reliable and efficient detection of the presence of fluid to be aerosolised. Further, the invention aims to provide a method of operating such an aerosol delivery device. These goals are achieved by a device with the technical features of claim 1 and by a method with the technical features of claim 14. Preferred embodiments of the invention follow from the dependent claims.

The invention provides an aerosol delivery device comprising an aerosol generator for generating an aerosol in the aerosol delivery device with a membrane, e.g., a vibratable or oscillatable membrane, and a vibrator, vibration generator or oscillator which is configured to vibrate or oscillate a fluid or liquid and to aerosolise the fluid or liquid by the membrane. The aerosol delivery device further comprises a fluid or liquid reservoir for receiving the fluid or liquid to be aerosolised or nebulised, the fluid or liquid reservoir being arranged in fluid communication with the vibratable membrane, a controller which is configured to operate the vibrator, vibration generator or oscillator so as to vibrate the fluid or liquid, and a temperature sensor which is configured to detect, sense or measure a temperature of the vibrator, vibration generator or oscillator and/or the membrane. Moreover, the aerosol delivery device comprises a detector which is configured to detect or determine the presence of fluid or liquid in contact with the membrane and/or in the fluid or liquid reservoir on the basis of the temperature of the vibrator and/or the membrane detected by the temperature sensor.

The detector is configured to detect or determine the presence of fluid or liquid in contact with the membrane and/or in the fluid or liquid reservoir, i.e., the presence of fluid or liquid to be aerosolised in the fluid or liquid reservoir.

The controller is configured to operate the vibrator so as to vibrate the fluid or liquid by supplying power, such as an electrical drive signal, to the vibrator.

If fluid or liquid to be aerosolised is present in the fluid or liquid reservoir, heat, such as Joule heat, generated by the vibrator, due to the power supplied to the vibrator, is transferred to the fluid or liquid, thus maintaining the vibrator at a substantially constant temperature. If no fluid or liquid to be aerosolised is present in the fluid or liquid reservoir, heat flux is diminished and the vibrator heats up, also resulting in an increase of the temperature of the membrane.

Such a temperature increase of the vibrator and the membrane occurs if no fluid or liquid to be aerosolised is present, substantially independently on the structural details of the aerosol generator, such as the exact configuration of the aerosol generator and production deviations or variations. Thus, the presence of fluid in contact with the membrane and/or in the fluid reservoir can be detected or determined in a reliable and efficient manner and with a high degree of accuracy. Further, the presence of fluid in contact with the membrane and/or in the fluid reservoir can be detected or determined in a simple way.

The fluid or liquid reservoir may be arranged for directly receiving the fluid or liquid to be aerosolised. For example, the fluid or liquid reservoir may be configured as a fluid or liquid chamber or container into which a fluid or liquid can be directly filled.

Further, the fluid or liquid reservoir may be arranged for receiving a fluid or liquid containing vessel. In particular, the fluid or liquid reservoir may be designed so that it does not directly receive the fluid or liquid but rather has an opening element, such as a thorn, a spike, a hollow needle or the like, arranged on its inside that opens the fluid containing vessel, e.g., a vial, a blister, an ampoule, a container, a canister, a reservoir, a cartridge, a pot, a tank, a pen, a storage, a syringe or the like, inserted therein.

The detector may form part of the controller or may be provided as a separate unit or entity. The temperature sensor may form part of the controller or may be provided as a separate unit or entity. The detector and the temperature sensor may be provided as a combined unit or entity or as separate units or entities. The temperature sensor and/or the detector may be connected to the controller. The detector and the temperature sensor may be connected with each other.

The controller may be any type of controller, e.g., a control unit, a control element, a control circuit or the like, which is capable of operating the vibrator of the aerosol generator. The controller may be connected to the vibrator, e.g., by a wiring or a cable or cables.

In some embodiments, the controller, which may be capable of operating the vibrator of the aerosol generator, may be wirelessly connected to the vibrator, e.g., by inductive coupling. For example, two coils may be used to transfer the electrical drive signal from the controller to the vibrator. The first coil may be arranged at the controller, e.g., at a control unit (controller setup component), and the second coil may be placed at the aerosol delivery device (vibrator setup component). The controller with the first coil may be configured to operate the vibrator with the second coil, e.g., by an electrical drive signal, to vibrate the vibrator and also to vibrate the adjoining fluid or liquid thereby.

The aerosol delivery device may be configured so that the process of detecting the presence of fluid to be aerosolised in the fluid reservoir is performed continuously or at discrete time intervals. The former of these two configurations is particularly preferred, allowing for especially reliable and efficient detection.

The aerosol delivery device may be an aerosol generation device, an aerosol inhalation device, a medical aerosol device, an aerosol diagnostic device, an aerosol prophylactic device, an aerosol therapeutic device, an aerosol humidification device, an aerosol therapy device or the like.

The aerosol generator may be a nebuliser, such as a vibrating membrane nebuliser, e.g. an electronic vibrating membrane nebuliser, an atomiser or the like. In particular, the aerosol generator may be an electronic nebuliser, e.g., a piezo-electrically driven nebuliser, i.e., a nebuliser driven by a piezoelectric element. In this case, the piezoelectric element may form part of the vibrator and be arranged for vibrating or oscillating the fluid.

The vibrator may comprise or consist of a piezoelectric element. The temperature sensor may be configured to detect the temperature of the piezoelectric element. The detector may be configured to detect the presence of fluid in contact with the membrane and/or in the fluid reservoir on the basis of the temperature of the piezoelectric element detected by the temperature sensor. This configuration allows for a particularly accurate detection of the presence of fluid to be aerosolised.

The vibrator or, for example, a piezoelectric element of the vibrator may be arranged at the side of the membrane which is in contact with the fluid or at the opposite side of the membrane, i.e., the side of the membrane to which the fluid is aerosolised. The latter of these two configurations is particularly preferred.

A fluid or liquid to be nebulised or aerosolised by the aerosol generator may be a fluid or liquid for the generation of a pharmaceutical aerosol for the delivery of an active compound.

An active compound is a natural, biotechnology-derived or synthetic compound or mixture of compounds useful for the diagnosis, prevention, management or treatment of a disease, condition or symptom of a mammal, in particular a human. Other terms which may be used as synonyms of active compounds include, for example, active ingredient, active pharmaceutical ingredient, drug substance, diagnostic material, drug, medicament and the like. The fluid could be of a liquid, solution, suspension, colloidal mixture or liposomal formulation form and can be prepared, mixed or opened before or during the application.

The active compound comprised in the fluid to be nebulised or aerosolised by the aerosol generator may be a drug substance or a medicament which is useful for the prevention, management, diagnosis or treatment of any disease, symptom or condition affecting the body, skin, body cavities, the abdomen, the eyes, the ear, the intestine, the stomach, the nose, the nasal cavities, the sinuses, the osteomeatal complex, the mouth, the trachea, the lungs, upper lungs, lower lungs, central lungs, the bronchia, the bronchioles, the alveoli and/or the respiratory tract. In particular, an aerosol may comprise an active compound which is useful for the prevention, management, diagnosis or treatment of any pulmonary or respiratory disease, symptom or condition. The active compound comprised in the fluid to be nebulised or aerosolised by the aerosol generator may be used especially for clinical trials or regulatory approvals.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, immunoglobulins, mucolytics, anti-allergic drugs, antihistaminics, mast-cell stabilising agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a suspension, a solution, a colloidal formulation (i.e., liposomal), etc.

Examples of potentially useful anti-inflammatory compounds are glucocorticoids and non-steroidal anti-inflammatory agents such as arformoterole, betamethasone, beclomethasone, budesonide, ciclesonide, dexamethasone, desoxymethasone, fluoconolone acetonide, fluocinonide, flunisolide, fluticasone (propionate), formoterole, fumarate, icomethasone, rofleponide, tiotropium, triamcinolone acetonide, fluocortin butyl, hydrocortisone, hydroxycortisone-17-butyrate, prednicarbate, 6-methylprednisolone aceponate, mometasone furoate, pirfenidone, dehydroepiandrosterone-sulfate (DHEAS), tartrate, umeclidinium, vilanterol, elastane, prostaglandin, leukotriene, bradykinin antagonists, non-steroidal anti-inflammatory drugs (NSAIDs), such as ibuprofen and acetylsalicylic acid (ASA), including any pharmaceutically acceptable salts, esters, isomers, stereoisomers, diastereomers, epimers, solvates or other hydrates, prodrugs, derivatives, or any other chemical or physical forms of active compounds comprising the respective active moieties and combinations thereof, such as for example LABA and LAMA combinations like aclidinium and formoterol.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are
penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);
cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, inlcuding vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals, antimycotics, fungicide or fungistatic, such as for example flucytosin, griseofulvin, tolnaftal, naftifin, terbinafin, amorolfin, ciclopiroxolamin, echinocandins, such as micafungin, caspofungin, anidulafungin, amphotericin B or variconazole;

nitrofurans, including nitrofurantoin and nitrofuranzone;

polyenes, including amphotericin B, natamycin, nystatin, flucytosine;

other antibiotics, including tithromycin, lincomycin, clindamycin, oxazolindiones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, formycin, pentamidine, and Fab-I-Inhibitors;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA based drugs;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds, including pirfenidone, dexpantenol, allantoin, vitamins, hyaluronic acid, alphaantitrypsin, anorganic and organic zinc salts/compounds, salts of bismuth and selen;

antifibrotic compounds, for example, pirfenidone;

interferones (alpha, beta, gamma), tumor necrosis factors, cytokines, interleukines;

immunomodulators, including immunosuppressive compounds, antibody (Ab), cytostatics and metastasis inhibitors;

immunosuppressive compounds, including glucocorticoids, cytostatics, antibodies, drugs acting on immunophilins or other drugs, such as interferons, opioids, TNF binding proteins or mycophenolate;

immunosuppressive compounds, including immunomodulating agents, or immunosuppressive agents or antirejection medications are compounds that may, for example, inhibit or prevent activity of the immune system, for example to prevent graft rejection;

immunosuppressive compounds, including drugs acting on immunophilins, such as ciclosporin, tacrolimus, sirolimus, everolimus, mycophenolic acid, also called mycophenolate or mycophenolate-mofetil, methotrexat, or azathioprine;

antibody (Ab), including polyclonal antibodies or monoclonal antibodies, such as for example immunoglobulin (Ig), immunoglobulin G (IgG), immunoglobulin A (IgA), or immunoglobulin M (IgM); as well as fragments of antibodies, also known as Fab (fragment, antigen-binding) region, complementarity determining regions (CDRs), Fc (Fragment, crystallizable) region, or Fc receptors;

cytostatics and metastasis inhibitors, including chemotherapeutic agents or anti-cancer drugs, such as alkylating agents, antimetabolite, antimicrotubuli agents, anthracyclines, cisplatin, cyclophosphamid, cytoskeletal disruptors (taxanes), epothilones, histone deacetylase inhibitors, ifosfamid, inhibitors of topoisomerase I+II, intercalating agents, kinase inhibitors, mitomycin, nucleotide analogs and precursor analogs, peptide antibiotics, platinum-based agents, retinoids, and vinca alkaloids and derivatives;

alkylating agents, such as nimustine, melphanlane, carmustine, lomustine, cyclophosphosphamide, mechlorethamine, dacarbazine, nitrosoureas, temozolomide (oral dacarbazine), ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

taxane, such as paclitaxel, abraxane, taxotere or docetaxel;

topoisomerase I inhibitors, such as topotecan or irinotecan;

topoisomerase II inhibitors, such as doxorubicin or etoposid;

intercelating agents, such as anthracyclines, like doxorubicin;

platinum-based agents, such as cisplatin, carboplatin, oxaliplatin, or satraplatin;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, docetaxel, gefitinib, vandetanib, erlotinib, poly-ADP-ribose-polymerase (PRAP) enzyme inhibitors, banoxantrone, gemcitabine, pemetrexed, bevacizumab, ranibizumab.

Examples of potentially useful mucolytics are DNase, P2Y2-agonists (denufosol), drugs affecting chloride and sodium permeation, such as sodium chloride (NaCl, e.g., 0.9%, 3%, 6%, 7% solutions), ectoine (1,4,5,6-tetrahydro-2-methyl-4-pyrimidinecarboxylic acid), N-(3,5-Diamino-6-chloropyrazine-2-carbony)-N'-{4-[4-(2,3-dihydroxy-propoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, surfactant, synthetic surfactant and recombinant surfactant proteins.

Examples of a pulmonary surfactant (derived from: surface active agent), which support pulmonary development, may be an exogenous pulmonary surfactant, or belong to the class of "modified natural" pulmonary surfactants, which are lipid extracts of minced mammalian lung or lung lavage. These preparations have variable amounts of SP-B and SP-C proteins and, depending on the method of extraction, may contain non-pulmonary surfactant lipids, proteins or other components. Some of the modified natural pulmonary surfactants present on the market, like Survanta™, are spiked with synthetic components such as tripalmitin, dipalmitoylphosphatidylcholine and palmitic acid.

Examples of current modified natural pulmonary surfactants include, but are not limited to, bovine lipid pulmonary surfactant (BLES™, BLES Biochemicals, Inc. London, Ont), calfactant (Infasurf™, Forest Pharmaceuticals, St. Louis, Mo.), bovactant (Alveofact™, Thomae, Germany), bovine pulmonary surfactant (Pulmonary surfactant TA™, Tokyo Tanabe, Japan), and beractant (Survanta™, Abbott Laboratories, Inc., Abbott Park, Ill.).

Examples of pulmonary surfactants, which may belong to the class of "artificial" pulmonary surfactants, are simply mixtures of synthetic compounds, primarily phospholipids and other lipids that are formulated to mimic the lipid composition and behaviour of natural pulmonary surfactant and are devoid of pulmonary surfactant proteins, are artificial surfactants include, but are not limited to, pumactant (Alec™, Britannia Pharmaceuticals, UK), and colfosceril palmitate (Exosurf™, GlaxoSmithKline, plc, Middlesex).

Examples of pulmonary surfactants, which may belong to the class of "reconstituted" pulmonary surfactants, are artificial pulmonary surfactants to which have been added pulmonary surfactant proteins/peptides isolated from animals or proteins/peptides manufactured through recombinant technology such as those described in WO 95/32992, or synthetic pulmonary surfactant protein analogues such as those described in WO 89/06657, WO 92/22315 and WO 00/47623, are reconstituted surfactants include, but are not limited to, poractant alfa (Curosurf™ Chiesi Farmaceutici S.p.A.) and lucinactant (Surfaxin™, Windtree Therapeutics, Inc., Warrington, Pa.) and the product having the composition disclosed in WO 2010/139442.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents or anti-asthma compounds include the afore-mentioned glucocorticoids, cromolyn sodium, nedocromil, cetrizin, loratidin, montelukast, roflumilast, ziluton, omalizumab, heparinoids and other antihistamine, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine and long-acting beta-agonists (LABAs), such as Albuterol sulphate, formoterol fumarate, salmeterol xinafoate, arformoterol tartrate, and olodaterol.

Examples of potentially useful muscarinic antagonists are muscarine and nicotine, such as ipratropium bromide and acetylcholine as well as long-acting muscarinic antagonists (LAMA) such as aclidinium (bromide), glycopyrronium (bromide), ipratropium, tiotropium (bromide), and umeclidinium (bromide).

Examples of xanthine derived agents include theophylline, theobromine, caffeine.

Examples of PDE5-Inhibitors include sildenafil.

Examples of antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus by, AVE-7279 to treat asthma and allergies, TPI-ASM8 to treat allergic asthma, 1018-ISS to treat cancer. Examples of potentially useful peptides and proteins include antibodies against toxins produced by microorganisms, antimicrobial peptides such as cecropins, defensins, thionins, and cathelicidins.

Examples of radioactive agents for diagnoses or clinical trials are technetium 99m [Tc99, Technegas, Technetium (99mTc), Technetium-99 (99Tc)], krypton (81mKr) inhalation gas, and Xenon-133 [Xenon Xe-133]. A number of isotopes, such as iodine-131 (131I), phosphorous-32 (32P), strontium-90 (90Sr), and yttrium-90 (90Y), may be used. Especially for a pulmonary ventilation and blood perfusion (V/Q) diagnose scan or scintigraphic pulmonary deposition studies the isotopes, krypton (81mKr) inhalation gas or technetium 99m (99mTc), may be used.

Examples of potentially useful opioids are endogenous opioids, opium alkaloids and derivatives, synthetic opioids, allosteric modulators, and opioid antagonists.

The aerosol generator, such as a nebuliser, may be used with fluids or liquids of the groups of viral gene therapy agents or non-viral gene therapy agents. The transferred nucleotide constructs may be single or double stranded DNA, RNA, or siRNA. In one study, the gene therapeutic agent carries especially the CF gene to substitute and cure the cystic fibrosis deficiency. For the transfer to the patient, the substitute is integrated in a viral vector and masked in liposomes. The, from UK CF Gene Therapy Consortium (GTC) called, inhalative gene therapeutic agent "pGM169/ GL67A" is under clinical evaluation.

The detector may be configured to determine that no fluid in contact with the membrane and/or in the fluid reservoir is present if the temperature of the vibrator and/or the membrane detected by the temperature sensor exceeds a threshold value. In this way, a particularly simple and cost-efficient configuration of the aerosol delivery device can be achieved.

The threshold value may be stored in the detector, e.g., in a memory, such as RAM and/or flash, of the detector.

The detector may comprise a processor, such as a CPU, or the like which is configured to determine whether the threshold value has been exceeded. The detector may only comprise a comparator, e.g., an electronic comparator circuit, for example as a simplified setup, safety shutdown or secondary safety shutdown. The detector may comprise a processor and a comparator.

The detector may be configured to detect the presence of fluid in contact with the membrane and/or in the fluid reservoir on the basis of a change in the temperature of the vibrator and/or the membrane detected by the temperature sensor over a unit time interval. The detector may be configured to detect the presence of fluid in contact with the membrane and/or in the fluid reservoir on the basis of a temperature time gradient of the vibrator and/or the membrane. Such a configuration allows for detection of the presence of fluid to be aerosolised with a particularly high degree of accuracy.

The detector may be configured to determine that no fluid in contact with the membrane and/or in the fluid reservoir is present if the change in the temperature of the vibrator and/or the membrane over the unit time interval, e.g., the absolute value of this change, or the temperature time gradient of the vibrator and/or the membrane, e.g., the absolute value of this gradient, exceeds a threshold value.

The threshold value may be stored in the detector, e.g., in a memory, such as RAM and/or flash, of the detector.

The detector may comprise a processor, such as a CPU, or the like which is configured to determine whether the threshold value has been exceeded. The detector may only comprise a comparator, e.g., an electronic comparator circuit, for example as a simplified setup, safety shutdown or second safety shutdown. The detector may comprise a processor and a comparator.

The detector may be configured to detect the presence of fluid in contact with the membrane and/or in the fluid reservoir on the basis of a comparison between the temperature of the vibrator and/or the membrane detected by the temperature sensor and an ambient temperature. In this way, the influence of ambient temperature variations or fluctuations on the detection process can be minimised or even eliminated, thus further enhancing the detection accuracy.

For example, the aerosol delivery device may comprise an additional, second temperature sensor which is configured to detect the ambient temperature.

The detector may be configured to determine that no fluid in contact with the membrane and/or in the fluid reservoir is present if a difference between the temperature of the vibrator and/or the membrane detected by the temperature sensor and the ambient temperature, e.g., the absolute value of this difference, exceeds a threshold value.

The threshold value may be stored in the detector, e.g., in a memory, such as RAM and/or flash, of the detector.

The detector may comprise a processor, such as a CPU, or the like which is configured to determine whether the threshold value has been exceeded.

The vibrator may comprise a power supplying wiring. The power supplying wiring may be made of a metal, such as copper.

The controller may be configured to supply power, such as an electrical drive signal, to the vibrator through the power supplying wiring. This electrical drive signal may be transferred from the controller to the vibrator through electrically conducting, e.g., via a wire, electrical conductors, or inductive coupling, e.g., via two coils and wires.

The temperature sensor may be configured to detect the temperature of the power supplying wiring. The detector may be configured to detect the presence of fluid in contact with the membrane and/or in the fluid reservoir on the basis of the temperature of the power supplying wiring detected by the temperature sensor.

Electrical conductors, such as metals, in particular, copper, generally are also good thermal conductors. If no fluid or liquid to be aerosolised is present in the fluid or liquid reservoir, causing the vibrator to heat up, heat is thus conducted through the power supplying wiring, resulting in a temperature increase of the power supplying wiring. Hence, the temperature of the vibrator and/or the membrane can be detected by detecting the temperature of the power supplying wiring.

Detecting the temperature of the vibrator and/or the membrane by detecting the temperature of the power supplying wiring allows for the temperature sensor or, for example, a temperature sensing element or temperature sensing elements of the temperature sensor to be arranged or disposed at a distance from the fluid to be aerosolised, e.g., outside a body of the aerosol generator or a body of the aerosol delivery device. Therefore, a particularly simple configuration of the aerosol delivery device can be achieved. Further, the temperature sensor or, for example, the temperature sensing element or elements of the temperature sensor can be arranged or disposed in a particularly secure or protected position. Hence, the service life of the temperature sensor can be improved.

The aerosol delivery device may further comprise an electrical parameter sensor which is configured to detect at least one electrical parameter of the vibrator, e.g., an electronic phase shift of a piezoelectric element of the vibrator may be detected.

The at least one electrical parameter may be the voltage and/or the current and/or the power and/or the current/ voltage phase shift. For example, the at least one electrical parameter may be the current consumption, the current drain, the current draw or the like of the vibrator. The at least one electrical parameter may be the voltage drop or voltage consumption at the vibrator, e.g., at a piezoelectric element of the vibrator. The at least one electrical parameter may be the voltage applied to the vibrator, e.g., by the controller.

Each of these electrical parameters allows for a reliable and efficient detection of the presence of fluid in contact with the membrane and/or in the fluid reservoir. Moreover, these parameters can be detected, sensed or measured in a simple way, e.g., by using one or more current and/or voltage sensors, in a direct or in an indirect sensing method.

The detector may be configured to detect the presence of fluid in contact with the membrane and/or in the fluid reservoir on the basis of the temperature of the vibrator and/or the membrane detected by the temperature sensor and of the at least one electrical parameter of the vibrator detected by the electrical parameter sensor. In this way, the detection accuracy can be further enhanced. In particular, the risk of an erroneous determination that no fluid to be aerosolised is present in the fluid reservoir can be minimised or even eliminated.

For example, the detector may be configured so that, if the detector determines that no fluid in contact with the membrane and/or in the fluid reservoir is present on the basis of the temperature of the vibrator and/or the membrane detected by the temperature sensor, this determination is verified or confirmed by detecting the presence of fluid in contact with the membrane and/or in the fluid reservoir on the basis of the at least one electrical parameter of the vibrator detected by the electrical parameter sensor. The detector may be configured so that only if both of these detection processes yield the result that no fluid in contact with the membrane and/or in the fluid reservoir is present, it is concluded or determined that no fluid to be aerosolised is present in the fluid reservoir.

Alternatively, the detector may be configured so that these two detection processes are performed in reverse order, i.e., so that detection based on the at least one electrical parameter is carried out first, followed by detection based on the temperature of the vibrator and/or the membrane.

The detection process based on the at least one electrical parameter may be performed, e.g., in the manner disclosed in EP 1 558 315 A1 and/or in the manner disclosed in WO 2015/091356 A1.

For example, the controller may be configured so that, when detection on the basis of the at least one electrical parameter is carried out, it sequentially operates the vibrator at a plurality of different vibration frequencies. The electrical parameter sensor may be configured to detect the at least one electrical parameter of the vibrator for each of the plurality of different vibration frequencies. The detector may be configured to detect the presence of fluid in contact with the membrane and/or in the fluid reservoir on the basis of the dependence of the detected values of the at least one electrical parameter on the vibration frequency.

The detector may be configured to detect the presence of fluid in contact with the membrane and/or in the fluid reservoir on the basis of the temperature of the vibrator and/or the membrane which has been detected by the temperature sensor only during inhalation of a user of the aerosol delivery device, or only during exhalation of a user of the aerosol delivery device, or only during a period between inhalation and exhalation of a user of the aerosol delivery device. In this way, any influence of the breathing pattern of the user on the detection process can be minimised or even eliminated, thus further enhancing the detection accuracy.

For example, the aerosol delivery device may further comprise a flow sensor, a pressure sensor or the like for detecting exhalation and/or inhalation of a user of the aerosol delivery device and/or detecting a period between inhalation and exhalation of the user.

The controller may be configured to operate the vibrator at a substantially constant vibration frequency or at a constant vibration frequency. In this manner, temperature variations or fluctuations which may occur at the vibrator and/or the membrane in the case of vibration frequency changes are reliably avoided. Thus, a further improvement in detection accuracy can be achieved.

The temperature sensor may be an electrical temperature sensor, such as a thermocouple, a resistance thermometer or a silicon bandgap temperature sensor. The temperature sensor may be an integrated circuit temperature sensor.

The temperature sensor may comprise or consist of a thermistor. Thermistors are thermally sensitive resistors which exhibit a large, well-defined and precise change in electrical resistance when subjected to a temperature change. By using a temperature sensor comprising or consisting of a thermistor, an aerosol delivery device with a simple configuration and a high degree of detection accuracy can be provided in a particularly cost-efficient manner.

The temperature sensor may comprise or consist of a Negative Temperature Coefficient (NTC) thermistor. Such a thermistor exhibits a decrease in electrical resistance when subjected to a temperature increase. The temperature sensor may comprise or consist of a Positive Temperature Coefficient (PTC) thermistor. Such a thermistor exhibits an increase in electrical resistance when subjected to a temperature increase.

Particularly preferably, the temperature sensor comprises or consists of a Negative Temperature Coefficient (NTC) thermistor.

The controller may be configured to deactivate, e.g., automatically deactivate, the vibrator if no presence of fluid in contact with the membrane and/or in the fluid reservoir is detected by the detector. In this way, a user of the aerosol delivery device is provided with a clear indication that no fluid in contact with the membrane and/or in the fluid reservoir is present. Thus, complete dosage delivery is ensured and the aerosol dosage accuracy is increased, thereby improving the efficiency of the aerosol treatment. Further, by deactivating the vibrator, the power consumption of the aerosol generator can be minimised, e.g., increasing the lifetime of a battery in the aerosol delivery device. This may also improve the patient adherence and patient compliance due to rapid and reliable "end of treatment" indication to the patient or user.

The controller may be configured to output a signal, such as a tactile signal, an audio signal, an optical signal, such as a flashlight, or the like, if no presence of fluid or liquid in contact with the membrane and/or in the fluid reservoir is detected by the detector. In this way, the user's attention is immediately drawn to the absence of fluid in contact with the membrane and/or in the fluid reservoir.

The aerosol delivery device may comprise a signal emitting means for emitting a signal, such as a tactile signal, an audio signal, an optical signal, such as a flashlight, or the like, indicating that no fluid in contact with the membrane and/or in the fluid reservoir is present. The signal emitting means may be electrically connected to the temperature sensor, e.g., via a connecting line. The signal emitting means may be electrically connected to the controller or form part of the controller.

The membrane may be a passive membrane. The vibrator may be configured to vibrate a fluid supply system and/or a membrane back space of the aerosol delivery device.

The membrane may be an active membrane, e.g., a vibratable or oscillatable membrane. The vibrator may be configured to vibrate the membrane.

The invention further provides a method of operating an aerosol delivery device. The aerosol delivery device comprises an aerosol generator for generating an aerosol in the aerosol delivery device. The aerosol generator comprises a membrane and a vibrator. The vibrator is configured to vibrate a fluid and to aerosolise the fluid by the membrane. The aerosol delivery device further comprises a fluid reservoir for receiving the fluid to be aerosolised, wherein the fluid reservoir is arranged in fluid communication with the membrane. The method comprises the steps of operating the vibrator so as to vibrate the fluid, detecting a temperature of the vibrator and/or the membrane, and detecting the presence of fluid in contact with the membrane and/or in the fluid reservoir on the basis of the detected temperature of the vibrator and/or the membrane.

The method of the invention provides the technical effects and advantages already described in detail above for the aerosol delivery device of the invention. In particular, the method enables a reliable and efficient detection of the presence of fluid in contact with the membrane and/or in the fluid reservoir.

The features described above for the aerosol delivery device of the invention also apply to the method of the invention.

The method of the invention may be a method of operating the aerosol delivery device of the invention.

The vibrator may comprise or consist of a piezoelectric element. The method may comprise detecting the temperature of the piezoelectric element. The presence of fluid in contact with the membrane and/or in the fluid reservoir may be detected on the basis of the detected temperature of the piezoelectric element.

The presence of fluid in contact with the membrane and/or in the fluid reservoir may be detected on the basis of a change in the detected temperature of the vibrator and/or the membrane over a unit time interval.

The presence of fluid in contact with the membrane and/or in the fluid reservoir may be detected on the basis of a comparison between the detected temperature of the vibrator and/or the membrane and an ambient temperature.

The vibrator may comprise a power supplying wiring. The method may comprise detecting the temperature of the power supplying wiring. The presence of fluid in contact with the membrane and/or in the fluid reservoir may be detected on the basis of the detected temperature of the power supplying wiring.

The method may further comprise detecting at least one electrical parameter of the vibrator.

The presence of fluid in contact with the membrane and/or in the fluid reservoir may be detected on the basis of the detected temperature of the vibrator and/or the membrane and of the detected at least one electrical parameter of the vibrator.

The detection step based on the detected at least one electrical parameter may be performed, e.g., in the manner disclosed in EP 1 558 315 A1 and/or in the manner disclosed in WO 2015/091356 A1.

The presence of fluid in contact with the membrane and/or in the fluid reservoir may be detected on the basis of the temperature of the vibrator and/or the membrane which has been detected only during inhalation of a user of the aerosol delivery device, or only during exhalation of a user of the aerosol delivery device, or only during a period between inhalation and exhalation of a user of the aerosol delivery device.

In the method of the invention, the vibrator may be operated at a constant vibration frequency.

The method may further comprise the step of deactivating, e.g., automatically deactivating, the vibrator if no presence of fluid in contact with the membrane and/or in the fluid reservoir is detected.

The method may further comprise the step of outputting a signal, such as a tactile signal, an audio signal, an optical signal, such as a flashlight, or the like, if no presence of fluid in contact with the membrane and/or in the fluid reservoir is detected.

BRIEF DESCRIPTION OF THE DRAWINGS

Hereinafter, non-limiting examples of the invention are explained with reference to the drawings, in which.

DETAILED DESCRIPTION OF CURRENTLY PREFERRED EMBODIMENTS

Currently preferred embodiments of the present invention will now be described with reference to the accompanying drawings. The preferred embodiments relate to aerosol delivery devices and to methods of operating these devices.

In the following, a first embodiment of the aerosol delivery device of the present invention and of the operating method of the present invention will be described with reference to FIG. 1, and a second embodiment of the aerosol delivery device of the present invention and of the operating method of the present invention will be described with reference to FIG. 8.

Figure 1:
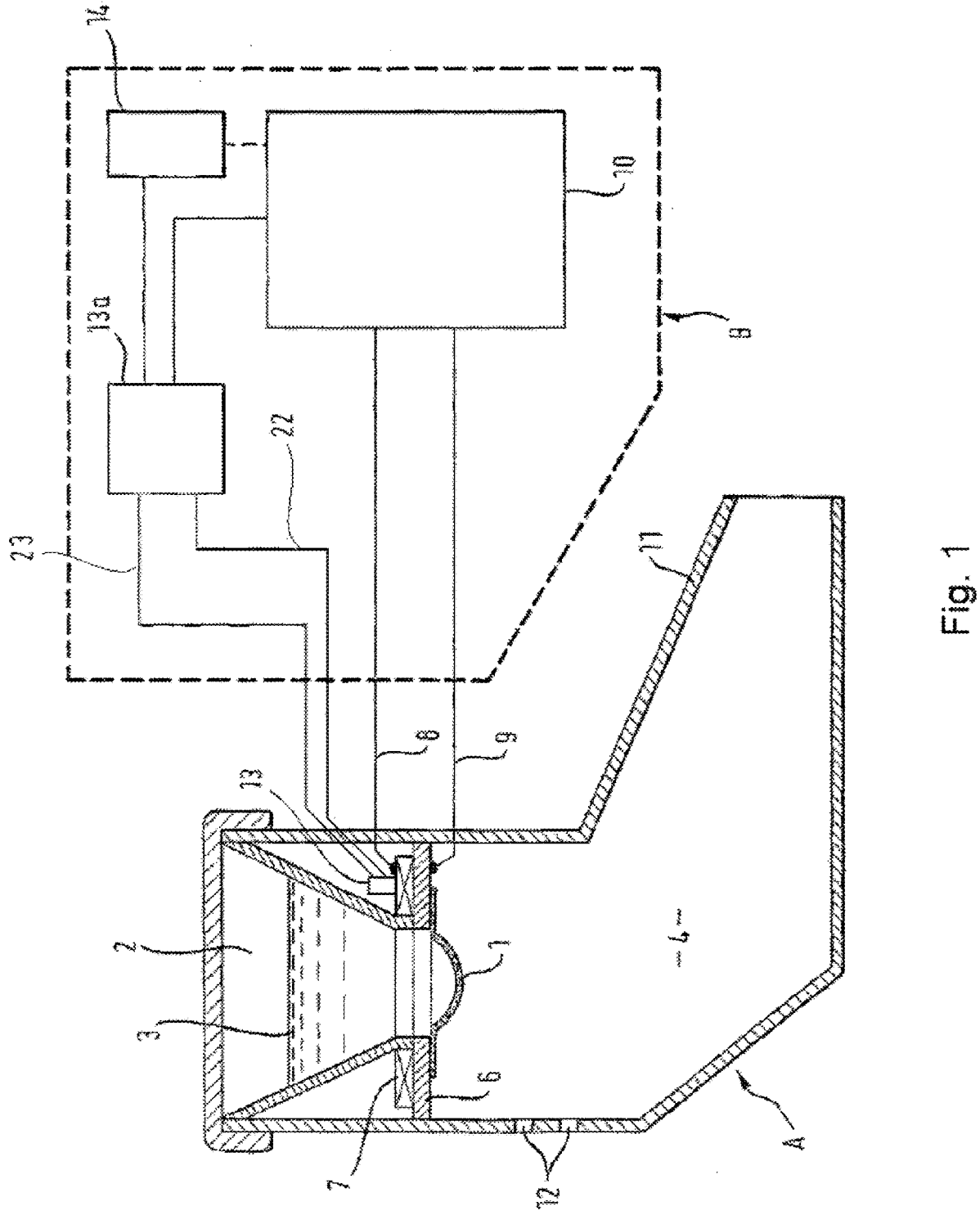
FIG. 1 shows a schematic longitudinally cut cross-sectional view of an aerosol delivery device according to an embodiment of the present invention.

FIG. 1 shows a schematic longitudinally cut cross-sectional view of an aerosol delivery device A according to an embodiment of the present invention. FIG. 8 shows a schematic longitudinally cut cross-sectional view of an aerosol delivery device A according to another embodiment of the present invention.

The aerosol delivery device A comprises an aerosol generator consisting of a vibratable membrane 1, a support unit 6 and a vibrator 7, e.g., an electromechanical transducer unit, such as a piezoelectric element, which is configured to vibrate the membrane 1. Particularly preferably, the vibrator 7 is a piezoelectric element. The membrane 1 is attached to the support unit 6 which supports the membrane 1 and to which the vibrator 7 is also attached. The aerosol delivery device A further comprises a fluid reservoir 2 for receiving a fluid 3 to be aerosolised, the fluid reservoir 2 being arranged in fluid communication with the membrane 1, and a controller 10 which is configured to operate the vibrator 7 so as to vibrate the membrane 1, thereby vibrating and aerosolising the fluid 3. The vibrator 7 is arranged at the side of the membrane 1 which is in contact with the fluid 3, i.e., at the side of the fluid reservoir 2. The controller 10 is configured to operate the vibrator 7 at a constant vibration frequency.

Moreover, the aerosol delivery device A comprises a temperature sensor 13 which is configured to detect, sense or measure a temperature of the vibrator 7, in particular, a temperature of a piezoelectric element forming part of the vibrator 7 or forming the vibrator 7. The temperature sensor 13 may be configured to detect the temperature of the vibrator 7 by detecting the temperature of a power supplying wiring of the vibrator 7 (see FIG. 8), as will be detailed below. In the present embodiments, the temperature sensor 13 is a thermistor. Specifically, the temperature sensor 13 is a Negative Temperature Coefficient (NTC) thermistor.

The control unit B comprises a detector 13a which is configured to detect or determine the presence of fluid 3 in contact with the membrane 1 on the basis of the temperature of the vibrator 7 detected by the temperature sensor 13.

The controller 10 is electrically connected to the vibrator 7 via a power supplying wiring. The power supplying wiring comprises connecting lines 8, 9. The controller 10 is configured to supply power, such as an electrical drive signal, to the vibrator 7 through the power supplying wiring, i.e., the connecting lines 8, 9.

Figure 2:
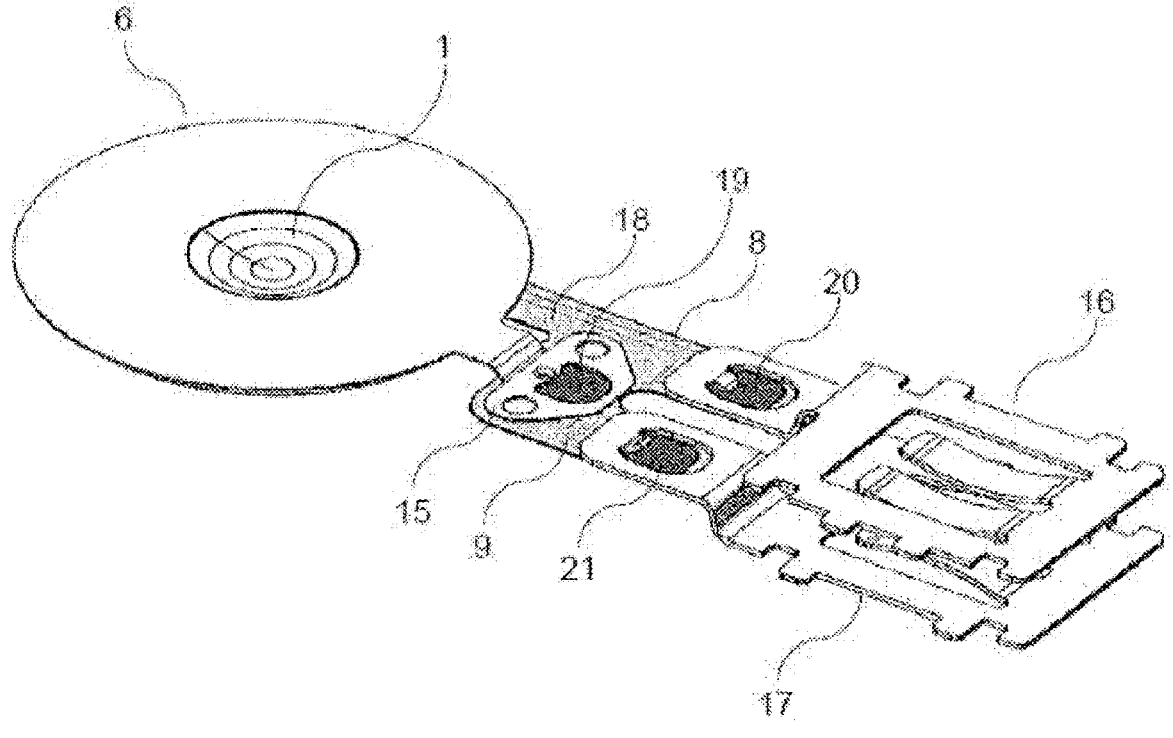
FIG. 2 shows a schematic perspective top view of a vibratable structure of an aerosol delivery device according to an embodiment of the present invention, the vibratable structure comprising a vibratable membrane, a support unit, a vibrator and a power supplying wiring.

The power supplying wiring may be in the form of power supplying lines, such as connecting lines 8, 9, on a circuit board, e.g., a circuit board comprising a Kapton substrate or the like (see FIG. 2). The power supplying lines, in particular, the connecting lines 8, 9, may be made of a metal, such as copper.

Figure 8:
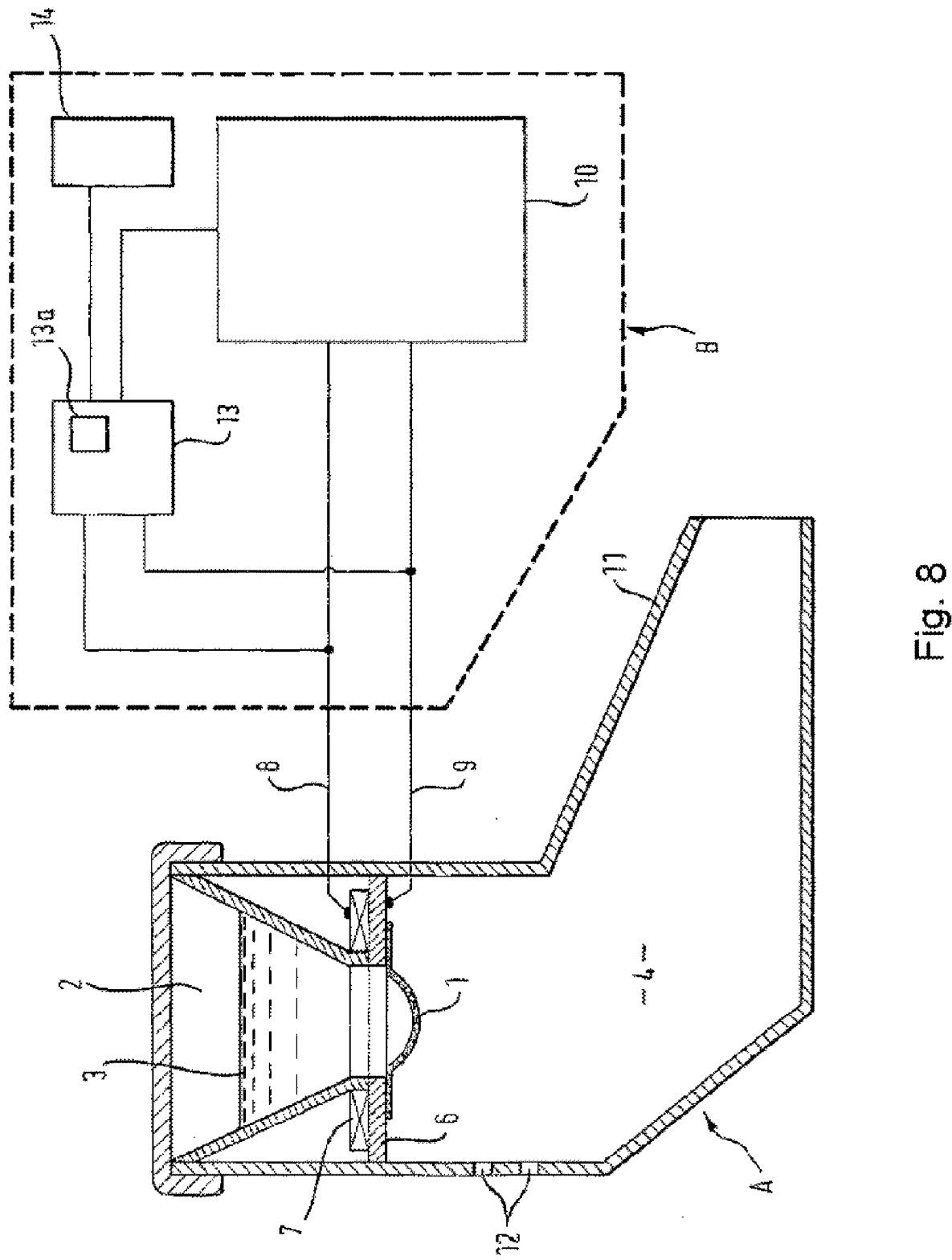
FIG. 8 shows a schematic longitudinally cut cross-sectional view of an aerosol delivery device according to an embodiment of the present invention.

The temperature sensor 13 is connected to the controller 10 via separate connecting lines, as is shown in FIGS. 1 and 8. In the embodiment shown in FIG. 1, these connecting lines include connecting lines 22, 23. Further, the control unit B comprises a signal emitting means 14 for emitting a signal, such as a tactile signal, an audio signal, an optical signal or the like, indicating that no fluid in contact with the membrane 1 is present. The signal emitting means 14 is electrically connected to the temperature sensor 13 and/or the detector 13a via a connecting line (see FIG. 1 and FIG. 8). Additionally or alternatively, the signal emitting means 14 may be electrically connected to the controller 10 (see FIG. 1).

The connecting lines 8, 9, 22 and/or 23 may also include an inductive coupling, e.g., at least two coils and a connecting wire. The at least two coils may be placed as counterparts on the control unit B (controller setup component) and on the aerosol delivery device A (vibrator setup component).

The membrane 1, the support unit 6 and the vibrator 7 are configured in a rotationally symmetrical manner in the embodiments described here and together form a vibratable or oscillatable structure.

The controller 10, the detector 13a and the signal emitting means 14 are accommodated together in the control unit B. The detector 13a may be integrated with the sensor 13, i.e., the sensor 13 and the detector 13a may be provided as a combined unit (see FIG. 8). The combined unit may be arranged in the aerosol delivery device A or in the control unit B.

The aerosol delivery device A further comprises a mixing chamber or aerosol cavity 4 in fluid communication with the membrane 1. The mixing chamber or aerosol cavity 4 is arranged on the side of the membrane 1 which is opposite to the membrane side facing the fluid reservoir 2. One or more air holes 12 are provided in the housing of the aerosol delivery device A. A mouthpiece or nosepiece 11 of the aerosol delivery device A is provided in fluid communication with the mixing chamber or aerosol cavity 4.

The mixing chamber or aerosol cavity 4 may contain, e.g., one or more inhalation valves and one or more exhalation valves (not shown). The aerosol generator may produce an aerosol cloud in the mixing chamber or aerosol cavity 4 during the exhalation phase, when the air (fluid) passes through the exhalation valve(s), and accumulate a high aerosol amount in the mixing chamber or aerosol cavity 4 for the next inhalation phase. In this case, the aerosol delivery device A works like a breath enhanced device, similar to an aerosol bolus, such as, e.g., disclosed in DE 19953317, EP 1227856, DE 102008054431 or EP 2361108.

In the following, examples of the operation of the aerosol delivery devices A shown in FIGS. 1 and 8, exemplifying embodiments of the method of the invention, will be explained.

The controller 10 supplies power, such as an electrical drive signal, to the vibrator 7 via the connecting lines 8, 9, causing the membrane 1 to vibrate. The fluid 3, e.g., a liquid, stored in the fluid reservoir 2 and abutting the membrane 1 is conveyed through holes or openings (not shown) in the vibrating membrane 1 and thereby aerosolised into the aerosol mixing chamber 4. The aerosol thus provided in the aerosol mixing chamber 4 can be inhaled by a user or patient through the mouthpiece or nosepiece 11 of the aerosol delivery device A. In order to supply a sufficient amount of air, ambient air can enter through the one or more air holes 12 into the aerosol mixing chamber 4 during inhalation. Further, the air exhaled by the patient or user can exit from the aerosol mixing chamber 4 through the one or more air holes 12 during exhalation.

If fluid 3 to be aerosolised is present in the fluid reservoir 2, heat, such as Joule heat, generated by the vibrator 7, due to the power supplied to the vibrator 7 by the controller 10, is transferred to the fluid 3, thus maintaining the vibrator 7 at a substantially constant temperature. If no fluid 3 to be aerosolised is present in the fluid reservoir 2, the temperature of the vibrator 7 increases. Thus, the presence of fluid 3 in the fluid reservoir 2 can be reliably and efficiently detected by monitoring the temperature of the vibrator 7.

This monitoring process is performed by the temperature sensor 13 which is configured to detect the temperature of the vibrator 7. Specifically, the temperature sensor 13 may be configured to detect the temperature of the vibrator 7 by detecting the temperature of the power supplying wiring, i.e., one or both of the connecting lines 8, 9. For this purpose, e.g., one or more temperature sensing elements of the temperature sensor 13 may be placed on or adjacent to one or both of the connecting lines 8, 9, as is indicated in FIG. 8. Since, in the embodiment shown in FIG. 8, the temperature of the vibrator 7 is detected by detecting the temperature of the power supplying wiring, the temperature sensor 13 can be arranged fully outside a body of the aerosol delivery device A (see FIG. 8).

The detector 13a which, in the embodiment of FIG. 1, is provided separately from the temperature sensor 13 detects the presence of fluid 3 in the fluid reservoir 2 on the basis of the temperature of the vibrator 7 detected by the temperature sensor 13 (see FIG. 1). In this embodiment, the temperature sensor 13 may be arranged on, at or adjacent to the vibrator 7 (see FIG. 1).

In the embodiment shown in FIG. 8, the detector 13a is integrally formed with the temperature sensor 13 and detects the presence of fluid 3 in the fluid reservoir 2 on the basis of the temperature of the vibrator 7 detected by the temperature sensor 13 as a combined unit. The combined unit of detector 13a and temperature sensor 13 may be arranged in the aerosol delivery device A (not shown) or in the control unit B (see FIG. 8).

The above-identified detection processes may be performed by the detector 13a in various different ways, as will be detailed in the following.

In some embodiments, such as the present embodiments, the detector 13a determines that no fluid 3 is present in the fluid reservoir 2 if the temperature of the vibrator 7 detected by the temperature sensor 13 exceeds a threshold value.

In some embodiments, the detector 13a determines that no fluid 3 is present in the fluid reservoir 2 if a change, over a unit time interval, in the temperature of the vibrator 7 detected by the temperature sensor 13, e.g., the absolute value of this change, or a temperature time gradient of the vibrator 7, e.g., the absolute value of this gradient, exceeds a threshold value.

In some embodiments, the detector 13a determines that no fluid 3 is present in the fluid reservoir 3 if a difference between the temperature of the vibrator 7 detected by the temperature sensor 13 and the ambient temperature, e.g., the absolute value of this difference, exceeds a threshold value. In this case, the aerosol delivery device A or the control unit B may comprise a second temperature sensor (not shown) which is configured to detect the ambient temperature.

The respective threshold values for the above-identified different detection approaches may be stored in the detector 13a, e.g., in a memory, such as RAM and/or flash, of the detector 13a. The detector 13a may comprise a processor, such as a CPU, or the like which is configured to determine whether the threshold value has been exceeded.

If the detector 13a determines that there is no fluid 3 present in the fluid reservoir 2, the detector 13a may emit a signal to the controller 10 which, in turn, automatically stops the supply of power to the vibrator 7, thereby automatically deactivating or switching off the aerosol delivery device A.

Alternatively or additionally, the detector 13a may instruct the signal emitting means 14 to emit a signal, such as a tactile signal, an audio signal, an optical signal or the like, to indicate to the patient or user that the aerosol delivery device A has consumed the fluid 3 stored in the fluid reservoir 2, which signals the end of the aerosol therapy session to the patient or user. In this case, the patient or user may then deactivate or switch off the aerosol delivery device A if no automatic deactivation or switch off function is provided in addition to the signal output. For example, an audio signal emitted for this purpose may be a short sound signal of 0.5 to 2 seconds in length.

In the following, a third embodiment of the aerosol delivery device of the present invention will be described with reference to FIGS. 2 and 3.

Figure 3:
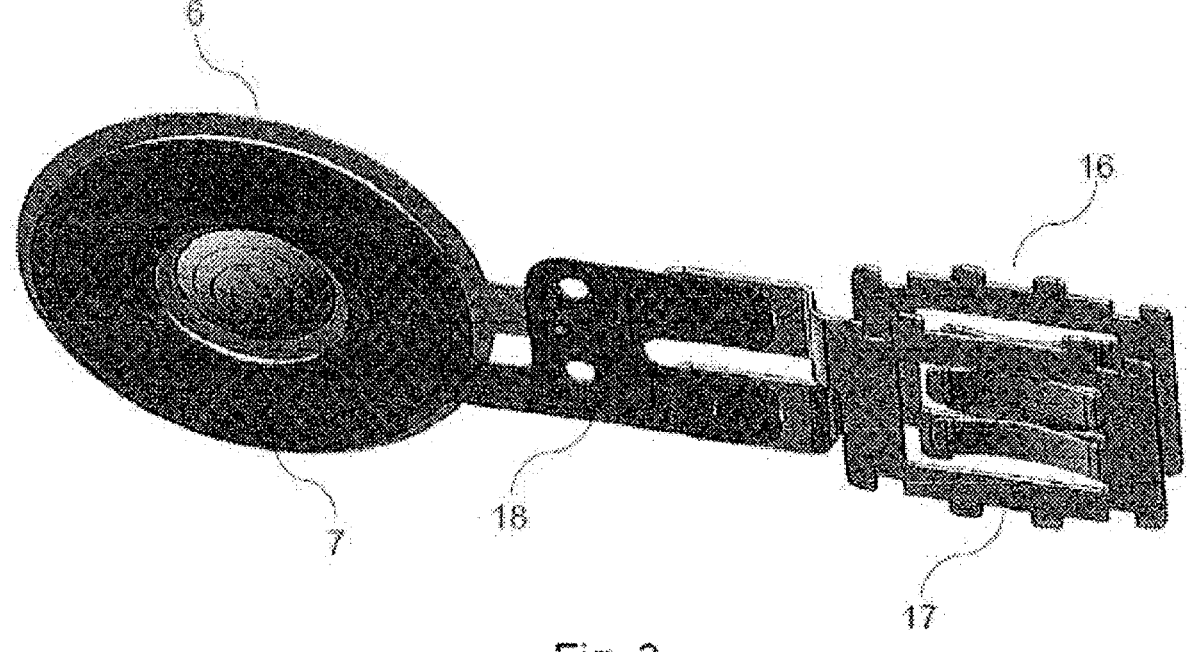
FIG. 3 shows a schematic perspective bottom view of the vibratable structure of the aerosol delivery device shown in FIG. 2.

The third embodiment of the invention substantially differs from the second embodiment of the invention only in that the vibrator 7 is arranged at the side of the membrane 1 to which the fluid 3 is aerosolised (see FIG. 3). Such an arrangement of the vibrator 7 is particularly preferred. The same reference signs are used for identical or similar components of the aerosol delivery devices of the first and second embodiments and a repeated description of these components is omitted.

FIG. 2 shows a schematic perspective top view of a vibratable structure of the aerosol delivery device according to the third embodiment of the present invention. This vibratable structure comprises a vibratable membrane 1, a support unit 6, a vibrator 7 (see FIG. 3) and a power supplying wiring in the form of connecting lines 8, 9 on a circuit board 18, such as a printed circuit board, further comprising a Kapton substrate or the like. The remaining part of the aerosol delivery device according to the third embodiment is identical to that of the aerosol delivery device A according to the second embodiment. FIG. 3 shows a schematic perspective bottom view of the vibratable structure of the aerosol delivery device shown in FIG. 2.

The vibrator 7 is an annular piezoelectric element arranged around the membrane 1, as is shown in FIG. 3. The vibrator 7 is attached, e.g., adhered, for example, using an adhesive, such as a glue, directly to the support unit 6.

The membrane 1 is integrally formed with the support unit 6. The membrane 1 and the support unit 6 are made of a metal, such as stainless steel. The support unit 6 is attached to the circuit board 18 through a connection member 15 of the support unit 6.

As is shown in FIG. 2, the vibratable structure further comprises a pair of electrical contacts 16, 17, e.g., plugs, for connection to the controller 10. The electrical contacts 16, 17 are punched out from a stainless steel sheet and subsequently bent, i.e., bent into the shape shown in FIG. 2. Both electrical contacts 16, 17 may have the same configuration, but the first contact 16 is rotated by 180° around its longitudinal axis relative to the second contact 17.

The electrical contacts 16, 17 are connected to the connection member 15 and the vibrator 7 through the circuit board 18. Specifically, the circuit board 18 has contact pads 19, 20, 21, e.g., gold contact pads, for connection with the electrical contacts 16, 17 and the connection member 15. The electrical contacts 16, 17 and the connection member 15 are secured to and electrically connected with the respective contact pads 19, 20, 21 of the circuit board 18 by welding, especially by resistance stud welding.

Further, the circuit board 18 is secured to and electrically connected with the vibrator 7, as is shown in FIG. 3, so that power can be supplied from the controller 10 to the vibrator 7 through the connecting lines 8, 9 of the circuit board 18.

The temperature sensor 13 (not shown in FIGS. 2 and 3) is configured to detect the temperature of the vibrator 7 by detecting the temperature of the power supplying wiring, i.e., one or both of the connecting lines 8, 9. For this purpose, e.g., one or more temperature sensing elements of the temperature sensor 13 may be placed on or adjacent to one or both of the connecting lines 8, 9. In particular, the one or more temperature sensing elements may be arranged on the circuit board 18, on or adjacent to one or both of the connecting lines 8, 9, in the region of the circuit board 18 between the contact pad 19 and the contact pads 20, 21.

The portion of the vibratable structure comprising the contact pads 19, 20, 21 may be encapsulated with a cover member (not shown), e.g., an electrically insulating cover member. The cover member may be made of a plastic material. The cover member may be provided so as to also cover the one or more temperature sensing elements of the temperature sensor 13. In this way, these elements can be particularly safely protected and isolated from external influences.

In some embodiments, the temperature sensor 13 may be configured to detect the temperature of the vibrator 7 at the electrical contacts 16, 17. In particular, one or more temperature sensing elements of the temperature sensor 13 may be arranged on one or both of the electrical contacts 16, 17.

Detection of the presence of fluid 3 in the fluid reservoir 2 on the basis of the temperature of the vibrator 7 detected by the temperature sensor 13 may be performed in the same manner as described above for the first and second embodiments, using the detector 13a.

FIGS. 4 to 7 show thermal images, taken by an infrared camera, of a portion of an aerosol generator of an aerosol delivery device according to an embodiment of the present invention. A vibratable structure of this aerosol generator substantially has the configuration shown in FIGS. 2 and 3. In particular, the thermal images of FIGS. 4 to 7 show the heat distribution of the vibrator 7. The temperatures given in the upper left corners of the thermal images are taken at the position indicated by a cross in the images. The measurement position is located on the lower right side of the circularly formed vibrator 7 (see FIGS. 4 to 7) on the circuit board 18. This measurement position is the same for all of the images.

Below the temperature, the emission ratio of copper ($\varepsilon$=0.94) is given in the upper left corners of the thermal images of FIGS. 4 to 7. An ideal conductor of heat, e.g., a black body, has an emission ratio of $\varepsilon$=1.00.

For the temperature measurements shown FIGS. 4 to 7, a saline solution was filled into a liquid reservoir of the aerosol delivery device first. Subsequently, the aerosol generator was operated so as to generate an aerosol by aerosolising the saline solution, thereby consuming the solution. During this process, the temperature of the portion of the aerosol generator was monitored by the infrared camera. FIGS. 4 to 7 show this temperature at different stages of this operation.

Figure 4:
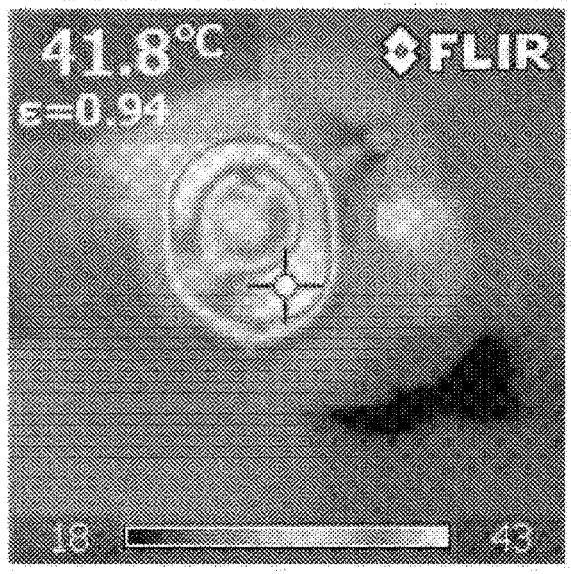
FIG. 4 shows a thermal image of a portion of an aerosol generator of an aerosol delivery device according to an embodiment of the present invention, wherein the image was taken in a state of the device in which liquid was present in a liquid reservoir of the device.
Figure 5:
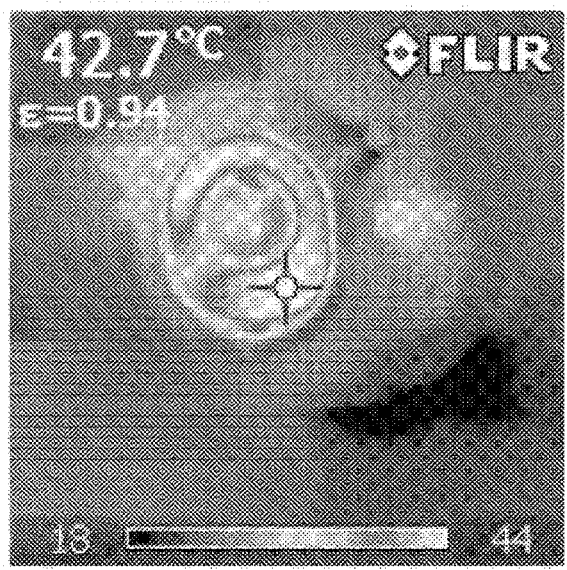
FIG. 5 shows a thermal image of the portion of the aerosol generator of FIG. 4, wherein the image was taken at a later time than the image shown in FIG. 4, in a state of the device in which less liquid was present in the liquid reservoir.

Specifically, FIGS. 4 and 5 show thermal images of the portion of the aerosol generator in a state of the aerosol delivery device in which saline solution was present in the liquid reservoir of the device. The thermal image of FIG. 5 was taken after that of FIG. 4, so that the amount of saline solution in the liquid reservoir had decreased. This is reflected by a small temperature increase from 41.8° C. (see FIGS. 4) to 42.7° C. (see FIG. 5).

Figure 6:
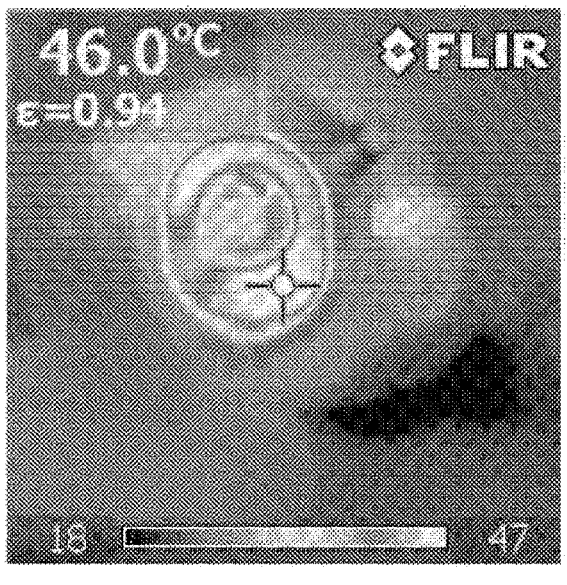
FIG. 6 shows a thermal image of the portion of the aerosol generator of FIG. 4, wherein the image was taken at a later time than the image shown in FIG. 5, in a state of the device in which no liquid was present in the liquid reservoir.

FIG. 6 shows a thermal image of the portion of the aerosol generator just after the saline solution in the liquid reservoir had been entirely consumed. Due to the absence of liquid in the reservoir, a significant temperature increase from 42.7° C. to 46.0° C. (see FIG. 6) was observed. The absence of liquid in the reservoir was measured as a temperature increase within 0.5 seconds.

Figure 7:
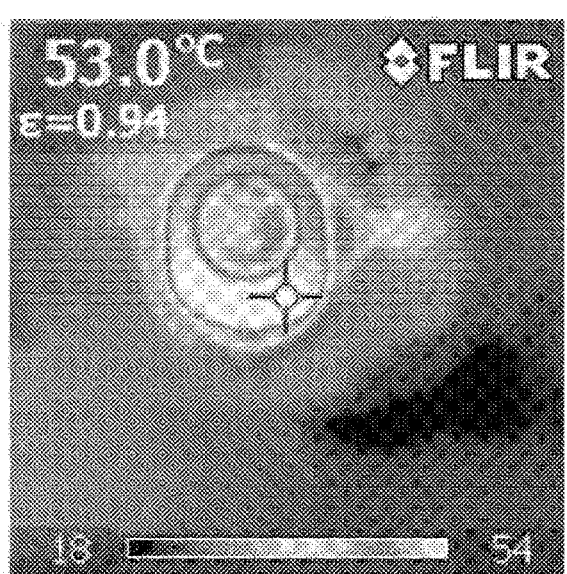
FIG. 7 shows a thermal image of the portion of the aerosol generator of FIG. 4, wherein the image was taken at a later time than the image shown in FIG. 6, also in a state of the device in which no liquid was present in the liquid reservoir.

Continued operation of the aerosol generator after full consumption of the saline solution resulted in a further considerable increase of the temperature to 53.0° C., as is shown in FIG. 7. This further temperature increase was measured within 1.0 seconds after the absence of liquid in the reservoir.

As is demonstrated by the thermal images shown in FIGS. 4 to 7, the temperature of the components of the aerosol generator, in particular, the vibrator 7 (as shown in FIG. 3), is a sensitive indicator for the presence of fluid or liquid in the fluid or liquid reservoir. Thus, detecting the presence of fluid or liquid on the basis of this parameter enables reliable and efficient detection with a high degree of accuracy.

The invention claimed is:

1. An aerosol delivery device comprising:
an aerosol generator for generating an aerosol in the aerosol delivery device, the aerosol generator comprising
a membrane, and
a vibrator which is configured to vibrate a fluid and to aerosolise the fluid by the membrane,
a fluid reservoir for receiving the fluid to be aerosolised, the fluid reservoir being arranged in fluid communication with the membrane,
a controller which is configured to operate the vibrator so as to vibrate the fluid, a temperature sensor which is configured to detect a temperature of the vibrator and/or the membrane, and
a detector which is configured to determine the presence of fluid in the fluid reservoir on the basis of the temperature of the vibrator and/or the membrane detected by the temperature sensor.

2. The aerosol delivery device according to claim 1, wherein the vibrator comprises a piezoelectric element, the temperature sensor is configured to detect the temperature of the piezoelectric element, and the detector is configured to determine the presence of fluid in contact with the membrane and/or in the fluid reservoir on the basis of the temperature of the piezoelectric element detected by the temperature sensor.

3. The aerosol delivery device according to claim 1, wherein the detector is configured to determine the presence of fluid in contact with the membrane and/or in the fluid reservoir on the basis of a change in the temperature of the vibrator and/or the membrane detected by the temperature sensor over a unit time interval.

4. The aerosol delivery device according to claim 1, wherein the detector is configured to determine the presence of fluid in contact with the membrane and/or in the fluid reservoir on the basis of a comparison between the temperature of the vibrator and/or the membrane detected by the temperature sensor and an ambient temperature.

5. The aerosol delivery device according to claim 1, wherein the vibrator comprises a power supplying wiring, the temperature sensor is configured to detect the temperature of the power supplying wiring, and the detector is configured to determine the presence of fluid in contact with the membrane and/or in the fluid reservoir on the basis of the temperature of the power supplying wiring detected by the temperature sensor.

6. The aerosol delivery device according to claim 1, further comprising an electrical parameter sensor which is configured to detect at least one electrical parameter of the vibrator.

7. The aerosol delivery device according to claim 6, wherein the detector is configured to determine the presence of fluid in contact with the membrane and/or in the fluid reservoir on the basis of the temperature of the vibrator and/or the membrane detected by the temperature sensor and of the at least one electrical parameter of the vibrator detected by the electrical parameter sensor.

8. The aerosol delivery device according to claim 1, wherein the detector is configured to determine the presence of fluid in contact with the membrane and/or in the fluid reservoir on the basis of the temperature of the vibrator and/or the membrane which has been detected by the temperature sensor only during inhalation of a user of the aerosol delivery device, or only during exhalation of a user of the aerosol delivery device, or only during a period between inhalation and exhalation of a user of the aerosol delivery device.

9. The aerosol delivery device according to claim 1, wherein the controller is configured to operate the vibrator at a constant vibration frequency.

10. The aerosol delivery device according to claim 1, wherein the temperature sensor comprises a thermistor.

11. The aerosol delivery device according to claim 1, wherein the controller is configured to deactivate the vibrator if no presence of fluid in contact with the membrane and/or in the fluid reservoir is determined by the detector.

12. The aerosol delivery device according to claim 1, wherein the membrane is a passive membrane and the vibrator is configured to vibrate a fluid supply system and/or a membrane back space of the aerosol delivery device.

13. The aerosol delivery device according to claim 1, wherein the membrane is an active membrane and the vibrator is configured to vibrate the membrane.

14. A method of operating an aerosol delivery device, the aerosol delivery device comprising:

an aerosol generator for generating an aerosol in the aerosol delivery device, the aerosol generator comprising a membrane, and a vibrator which is configured to vibrate a fluid and to aerosolise the fluid by the membrane, and a fluid reservoir for receiving the fluid to be aerosolised, the fluid reservoir being arranged in fluid communication with the membrane, the method comprising the steps of:

operating the vibrator so as to vibrate the fluid, detecting a temperature of the vibrator and/or the membrane, and determining the presence of fluid in the fluid reservoir on the basis of the detected temperature of the vibrator and/or the membrane.

15. The aerosol delivery device according to claim 1, wherein the detector is configured to determine the absence of fluid in contact with the membrane and/or in the fluid reservoir based on a detected temperature increase of the vibrator and/or the membrane.

16. The aerosol delivery device according to claim 1, wherein the detector is configured to determine the absence of fluid in contact with the membrane and/or in the fluid reservoir based on the detected temperature of the vibrator and/or the membrane exceeding a threshold value.

17. The aerosol delivery device according to claim 1, wherein the temperature sensor is in thermal contact with the membrane and/or the vibrator and/or power supplying wiring of the vibrator.

18. The aerosol delivery device according to claim 6, wherein the electrical parameter sensor is configured to detect an electrical parameter of a piezoelectric element of the vibrator.

* * * * *